United States Patent
Okazaki et al.

(10) Patent No.: US 7,195,675 B2
(45) Date of Patent: Mar. 27, 2007

(54) CHITOSAN-CONTAINING POLYSACCHARIDE, METHOD FOR PREPARING THE SAME AND USE THEREOF

(75) Inventors: Hideo Okazaki, Higashiyamato (JP); Tadao Hamaya, Bunkyo-ku (JP); Shoichi Kurihara, Koto-ku (JP)

(73) Assignee: Ricom Corporation, Tokyo (JP)

( * ) Notice: Subject to any disclaimer, the term of this patent is extended or adjusted under 35 U.S.C. 154(b) by 0 days.

(21) Appl. No.: 11/100,379

(22) Filed: Apr. 7, 2005

(65) Prior Publication Data

US 2005/0236328 A1 Oct. 27, 2005

Related U.S. Application Data

(63) Continuation of application No. PCT/JP2003/012920, filed on Oct. 8, 2003.

(30) Foreign Application Priority Data

Oct. 8, 2002 (JP) ............... 2002-295379

(51) Int. Cl.
    *C07H 3/02* (2006.01)
(52) U.S. Cl. ............ 127/29; 127/34; 210/634; 210/639; 210/774; 514/62; 536/55.2; 536/55.3; 536/124; 536/127; 536/128
(58) Field of Classification Search ............ 210/634, 210/638, 639, 774, 806; 127/29, 32, 65, 127/71, 34; 424/725, 195.15, 195.16, 780; 426/429, 481, 489, 615, 658; 514/54, 55, 514/62; 536/20, 55.2, 55.3, 123.1, 124, 127, 536/128; 435/101, 171, 254.1
See application file for complete search history.

(56) References Cited

U.S. PATENT DOCUMENTS

| 4,918,009 | A  | * | 4/1990  | Nilsson ............... 435/73 |
| 5,905,035 | A  | * | 5/1999  | Okada et al. ......... 435/254.1 |
| 6,255,085 | B1 | * | 7/2001  | Chen et al. .......... 435/101 |
| 6,485,946 | B1 | * | 11/2002 | Chen et al. .......... 435/101 |
| 6,759,049 | B2 | * | 7/2004  | Donatini ............. 424/195.15 |
| 6,972,284 | B2 | * | 12/2005 | Fan et al. ............ 435/254.1 |
| 7,049,433 | B2 | * | 5/2006  | Fan et al. ............ 536/55.2 |

FOREIGN PATENT DOCUMENTS

| EP | 381055 A1 | 8/1990 |
| EP | 976400 A1 | 2/2000 |

OTHER PUBLICATIONS

M. Noves-Ledieu et al., The cell walls of *Agaricus bisporus* and *Agaricus campestris* fruiting body hyphae, Canadian Journal of Microbiology, 1981, vol. 27, No. 8, pp. 779 to 787: p. 781, eight col., lines 12 to 23.
Valentina S. Gamayurova et al.; "Synthesis of Soluble Derivatives of Chitin-Glucane Complex"; Chemistry and Computational Simulation; Butlerov Communications; 1999; No. 1.
Natalia V. Shabrukova et al.; "Study of the Nature of Chitin-Glucan Bond in Chitin-Glucan Complex"; Chemistry and Computational Simulation; Butlerov Communications; 2001; No. 4.
Mariko Shida et al.; "Structure of the Alkali-Insoluble Skeletal Glucan of *Lentinus edodes*"; J. Biochem; vol. 90; pp. 1093-1100 (1981).
Robbert P. Hartland, et al.; "The Linkage of (1-3)-β-Glucan to Chitin During Cell Wall Assembly in *Saccharomyces cerevisiae*"; YEAST; vol. 10, pp. 1591-1599 (1994).

* cited by examiner

*Primary Examiner*—Joseph Drodge
(74) *Attorney, Agent, or Firm*—Sughrue Mion, PLLC

(57) ABSTRACT

The present invention herein provides a chitosan-containing polysaccharide and a method for the preparation thereof as well as a medicine and a food containing the polysaccharide.

The chitosan-containing polysaccharide is prepared by a method comprising the steps of heat-treating a fungus in a concentrated aqueous caustic alkali solution; subjecting the resulting solution to a solid-liquid separation treatment; dissolving the resulting solid contents in an aqueous organic acid solution; adding, to the resulting solution, an alcohol or a caustic alkali to thus form precipitates; washing the resulting precipitates; and then drying them. This chitosan-containing polysaccharide is a compound in which homopolymers of glucosamine are linked with glucan through covalent bonds; it has a molar ratio of glucosamine and glucose constituting the polysaccharide ranging from 1:5 to 5:1; it has a molecular weight of about 150,000; and it does not contain any $\beta(1 \rightarrow 3)$ bonds, but comprises $\beta(1 \rightarrow 4)$ bonds and $\beta(1 \rightarrow 6)$ bonds. The polysaccharide is free of any protein and reducing polysaccharide. The chitosan-containing polysaccharide is effective for the treatment or prevention of any diseases originated from living habits or customs such as hypertension and diabetes.

19 Claims, No Drawings

CHITOSAN-CONTAINING POLYSACCHARIDE, METHOD FOR PREPARING THE SAME AND USE THEREOF

CROSS REFERENCE TO RELATED APPLICATIONS

This is a continuation of PCT/JP2003/012920 filed on Oct. 8, 2003 and which claims priority from Japanese Patent Application No. 2002-295379 filed on Oct. 8, 2002, the above-noted applications incorporated herein by reference in their entirety.

TECHNICAL FIELD

The present invention relates to a novel chitosan-containing polysaccharide, a method for the preparation of the same and a pharmaceutical composition and a food, which contain the chitosan-containing polysaccharide as effective components thereof.

BACKGROUND ART

Up to this time, there have variously been investigated the characteristic properties of and methods for preparing chitosan derived from the crustaceans such as crabs and shrimps or lobsters (hereunder simply referred to as "crab chitosan"), but there has scarcely been investigated the chitosan originated from plants represented by fungi or mushrooms and methods for the preparation thereof and accordingly, there has scarcely been proposed any article concerning the same.

There have been proposed some research reports on chitosans produced by fungi such as bread mold (*Aspergillus niger*), *Saprolegnia* (*Achlya*) and *Actinomycetes*. However, it would be quite difficult to cultivate these fungi and there would be a strong probability that the cultivation product thereof may contain unknown toxic substances. Accordingly, the chitosan produced by the fungi could not be used in the applications in which the chitosan should satisfy the strict requirement for the safety to the human body.

On the other hand, it has been known that a trace amount of glucosaimine as a principal constituent of chitosan is included in the hydrophilic solvent extract (commercially sold under the trade name of "Champignon Extract") from a mushroom (*Agaricus bisporus*) which has been known to be effective in the treatment of nephropathy, but it has not yet been elucidated whether the trace glucosamine shows any physiological importance or not. Moreover, it has scarcely been tried to positively produce chitosan-containing polysaccharides starting from fungi including the mushroom (*Agaricus bisporus*).

In Asian district including Japan, fungi such as *Lentinus edodes, Auiricularia auriculal, Volvariella Speg* (*Volvariella volvacea*), *Lyophyllum Karst* (*Lyophyllum simeji*) and *Grifola frondosa* have long been used as excellent health foods extensively and widely and they have been considered to be food materials as the basis for ISHOKUDOGEN (both medicines and foods should be based on the same origin). In Europe, mushroom (champignon) (*Agaricus bisporus*) has widely been used as a food since the 17th century.

The term so-called "mushroom" or "champignon", in itself, generically means all kinds of fungi, but the term, in a narrow sense, means *Agaricus bisporus* cultivated in caverns in the suburbs of Paris since the 17th century. In this specification, however, to avoid the occurrence of any misunderstanding, mushroom or champignon is referred to as "*Agaricus bisporus*", while the term "fungs (or fungi)" is used for expressing the all kinds of edible mushrooms or champignon.

The annual output of the *Agaricus bisporus* in the world-wide scale amounts to 2,400,000 to 3,200,000 tons and this corresponds to 30 to 38% of the total output of the fungi cultivated in the whole world and the rate of the *Agaricus bisporus* cultivated in the united states is 90% of the total output of the fungi cultivated therein. From a historical standpoint, the chitin derived from plants was, for the first time, extracted from mushroom, as a high molecular weight substance insoluble in an alkali medium by Braconnot as a French botanist in 1811. In 1859, Rouget found that the chitin could be converted into a product soluble in an organic acid (solution) when it was heated in a concentrated potassium hydroxide solution and this substance is named as "chitosan" by Hoppe-Seyler in 1894.

A chitin-glucan compound was isolated from *Aspergillus niger* by Russian research workers during the term extending from 1999 to 2000. It was found that this chitin-glucan compound had a glucan content ranging from 15 to 20%. In this compound, the chitin and glucan are strongly linked to one another through a covalent bond and therefore, they can completely be hydrolyzed only through the treatment with an enzyme (see Non-patent Document Nos. 1 and 2 given below).

In 1981, Shida et al. reported the presence of a skeletal glucan, in *Lentinus edodes*, insoluble in an alkali medium (24%, at 5° C.). As a result of methylation analysis, it was found that the glucan moiety thereof had a structure consisting of sugar chains having highly branched β-1,6- and β-1,3-bonds. These glucans are bonded to chitin to thus form the internal skeleton of the *Lentinus edodes* (see Non-patent Document No. 3).

In 1994, Hartland et al. found that an alkali-soluble (1-3) β-glucan was converted into an alkali-insoluble (1-3) β-glucan through the formation of a linkage with chitin on the cell wall of *Saccharomyces cerevisiae* (see Non-patent Document No. 4).

It has been said that the constituents of the cell walls of fungi and mold are α(1-3) glucan and chitin, but polysaccharides are frequently reconstituted and or reorganized in these fungi during the process of the growth thereof. It has also been believed that the rates of the α- and β-structures vary during the growth cycle of *Agaricus bisporus*. More specifically, it has been recognized that the rate of β(1-4) increases during the proliferation process, while the rate of β(1-6) increases in the fruiting body thereof.

Even at present, however, the skeletal components of the fungi including chitin have not yet effectively been used, because of their high chemical stability and insolubility in water, dilute acid or alkali solutions or an organic solvent. One of the reasons therefor is that the chitin included in the fungi is insoluble in almost all of the solvents, that it is physiologically inactive, and that it has not been expected to have any usefulness as an ingredient for health foods and drugs.

Among the sugars originated from fungi, β-glucan as a water-soluble component of *Lentinus edodes* extracted with hot water was found to have immuno-enhancement effect and it has been investigated for use as an adjuvant. In addition, *Agaricus bisporus* has not chemically been investigated till quite recently, Ricom Corporation has, for the first time, proved that the extract thereof with hot water shows a deodorizing effect and the extract has now been put on the market as a deodorant.

As for most of the other fungi, some of them have been used in health foods as such, quite simply in the form of extracts with hot water or freeze-dried products, In this connection, examples of such other fungi include Coriolus versicolor, *Ganoderma lucidum* (REISHI) and *Agaricus bisporus* of Brazil growth.

Non-Patent Documet No. 1: Gamayurova et al., Synthesis of soluble derivatives of chitin-glucan complex. Chemistry and Computational Simulation. Butlerov Communicatios, 1999; No. 1.

Non-Patent Document No. 2: Shabrukova et al., Study of the nature of chitin-glucan complex. Chemistry and Computational Simulation. Butlerov Communicatios, 2001; No. 4.

Non-Patent Document No. 3: Shida et al., Structure of the alkali-insoluble skeletal glucan of *Lentinus edodes*. J-Biochem-Tokyo, 1981, 90(4):1093–1100.

Non-Patent Document No. 4: Hartland et al., The linkage of (1-3)-β-glucan to chitin during cell wall assembly in *Saccharomyces cerevisiae*. Yeast, 1994, 10(12):1591-1599.

DISCLOSURE OF THE INVENTION

Accordingly, it is an object of the present invention to provide a novel chitosan-containing polysaccharide.

It is another object of the present invention to provide a method for the preparation of the foregoing chitosan-containing polysaccharide and, in particular, to provide a method for effectively producing a chitosan-containing polysaccharide in a large quantity starting from chitin derived from safer fungi, which have widely been used as foods, such as those including, for instance, mushroom (*Agaricus bisporus*) and *Lentinus edodes*.

It is a still another object of the present invention to provide applications of such a chitosan-containing polysaccharide, in particular, as a drug and a food.

The details of the present invention are as follows:

1. A chitosan-contining polysaccharide having the following characteristic properties:
   (1) Constituent Saccharides: The polysaccharide comprises glucosamine and glucose and the molar ratio thereof ranges from 1:5 to 5:1;
   (2) Molecular Weight: The molecular weight thereof as determined according to the viscometric technique using an Ostwald viscometer ranges from about 50,000 to about 400,000. Moreover, the molecular weight thereof as determined according to the gel filtration chromatography technique ranges from about 40,000 to about 200,000;
   (3) Structural Units: The polysaccharide is mainly composed of chitosan moieties and glucan moieties;
   (4) Kinds of Linkages: The polysaccharide does not contain any β(1→3) bonds, but it comprises β(1→4) bonds and β(1→6) bonds;
   (5) Hydrolyzation with Enzyme: The polysaccharide is not hydrolyzed with a cellulase, but is hydrolyzed into oligosaccharides by the action of a chitosanase;
   (6) Proteins and Reducing Polysaccharides: The polysaccharide is free of any protein and reducing polysaccharide;
   (7) Color Reaction: It is negative to the iodo-starch reaction;
   (8) Color of the Substance: It is colorless (or it has a white color);
   (9) Solubility: It is soluble in an aqueous acetic acid, malic acid or ascorbic acid solution having a concentration ranging from 5 to 10% by mass, but it is insoluble in water, ethanol and an alkaline aqueous solution having a pH value of not less than 10.

2. The chitosan-containing polysaccharide as set forth in the foregoing item 1, wherein the molar ratio of the glucose and the glucosamine, which constitute the polysaccharide, is equal to 1:1.

3. The chitosan-containing polysaccharide as set forth in the foregoing item 1 or 2, wherein it has a chitosan content ranging from 18 to 72%.

4. The chitosan-containing polysacchide as set forth in any one of the foregoing items 1 to 3, wherein the chitosan moiety is a homopolymer of glucosamine.

5. The chitosan-containing polysaccharide as set forth in any one of the foregoing items 1 to 5, wherein the glucan moiety is a homopolymer of glucose.

6. A method for the preparation of a chitosan-containing polysaccharide as set forth in any one of the foregoing items 1 to 5, characterized in that it comprises the steps of heat-treating a fungus in an aqueous caustic alkali solution having a concentration ranging from 25 to 50% by mass; subjecting the resulting solution to a solid-liquid separation treatment; dissolving the resulting solid contents in an aqueous organic acid solution; adding, to the resulting solution, an alcohol or a caustic alkali to a pH value of not less than 10 to thus form precipitates; washing the resulting precipitates; and then drying them.

7. The method for the preparation of a chitosan-containing polysaccharide as set forth in the foregoing item 6, wherein the fugus is pre-treated with a cellulase or glucanase, prior to the heat-treatment thereof in the aqueous caustic alkali solution.

8. The method for the preparation of a chitosan-containing polysaccharide as set forth in the foregoing item 6 or 7, wherein the fungus is *Agaricus bisporus*.

9. A method for the preparation of a chitosan-containing polysaccharide as set forth in any one of the foregoing items 1 to 5, characterized in that it comprises the steps of heat-treating a fungus in an aqueous caustic alkali solution having a concentration ranging from 25 to 50% by mass; adjusting the viscosity of the solution to a level of 3 to 20 mPa·s; subjecting the resulting solution to a solid-liquid separation treatment; washing the resulting solid contents; and then drying the same.

10. The method for the preparation of a chitosan-containing polysaccharide as set forth in the foregoing item 9, wherein water or an acid is added to the solution obtained after the heat-treatment of the fungus in the aqueous caustic alkali solution to thus control the viscosity of the latter to a level of 3 to 20 mPa·s.

11. A pharmaceutical composition comprising, as an effective component, a chitosan-containing polysaccharide as set forth in any one of the foregoing items 1 to 5.

12. The pharmaceutical composition as set forth in the foregoing item 10 for use in the treatment or prevention of any diseases originated from living habits or customs.

13. A food comprising, as an effective component, a chitosan-containing polysaccharide as set forth in any one of the foregoing items 1 to 5.

The chitosan-containing polysaccharide of the present invention is completely free of any allergenic substances such as impurities, for instance, proteins and sulfur-containing compounds which are observed for or present in the crab chitosan and accordingly, it would be effective or useful as a novel functional foodstuff. Chitosan originated from the crustaceans, for instance, crab chitosan obtained starting from crabs may give out an offensive smell and disagreeable harshness peculiar to the crabs. On the other hand, when the chitosan-containing polysaccharide of the present invention is obtained from fungi as starting materials, it can emit an agreeable and pleasant fragrance peculiar to the fungi selected and accordingly, it is quite free of any disagreeable smell and offensive harshness. Moreover, the chitosan-containing polysaccharidie of the present invention includes about 50% of polysaccharides in addition to glucosamine and therefore, the polysaccharide of the invention may have novel physiological activities other than those observed for the crab chitosan.

A further advantage of the chitosan-containing polysaccharide is such that it is a polysaccharide-glucan whose constituent sugars are almost exclusively constituted from glucoses, unlike the chitosans isolated from the crustaceans such as crabs and shrimps.

BEST MODE FOR CARRYING OUT THE INVENTION

The present invention will hereunder be described in more detail.

We have taken notice of the presence of components soluble in an organic acid and insoluble in an alkaline solution among those present in the "Champignon Extract" derived from *Agaricus bisporus*, manufactured and sold by Ricom Corporation and used as a health food, have tried to analyze the components in detail, have found that they comprise polysaccharides having characteristic properties quite similar to those observed for chitosan, have conducted various studies on these components and have thus succeeded in the large-scale extraction of chitosan from *Agaricus bisporus*. The chitosan extracted from *Agaricus bisporus* has found to be a novel substance which has basic characteristic properties similar to those observed for the crab chitosan extracted from the crustaceans and which is different, in the component, from the latter in that the former comprises glucan-like polysaccharides. In this respect, the crab chitosan comprises a simple homopolymer consisting only of glucosamine.

In this specification, this novel substance will hereunder be referred as "chitosan-containing polysaccharide(s)".

From a historical point of view, it has been discovered, for the first time, that the chitosan is a substance or component present in "mushroom", but the subsequent researches therefor have been conducted exclusively using those derived from crustaceans and the term "chitosan" exclusively means crab chitosan. Further, as for the definition of chitosan, the crab chitosan is a simple polymer almost 100% of which is constituted by N-acetyl-glucosamine and therefore, it should satisfy such a requirement that not less than 80% of the acetyl groups thereof must be deacetylated. According to the intrinsic definition of chitosan, however, the term means a polysaccharide insoluble in a dilute alkaline solution and soluble in a dilute organic acid solution as has previously been discussed above. According to this definition, the chitosan derived from fungi would certainly be recognized as one falling within the family of chitosan.

The novel chitosan-containing polysaccharide of the present invention can be prepared from almost all kinds of fungi which have widely been used as foods or foodstuffs. Chitosan-containing polysaccharides likewise occur in nature in a trace quantity; but most of them are simply present in the form of chitin substances obtained through the formation of strong linkages with glucan and accordingly, only the method developed by the inventors of this invention would first be able to reveal the chitosan-containing polysaccharides in its entirety.

The method for the preparation of the chitosan-containing polysaccharide according to the present invention will be described below in detail.

Starting materials used for the preparation of the chitosan-containing polysaccharide of the invention are not restricted to particular ones inasmuch as they contain chitin-containing polysaccharides, but it is preferred to use vegetable substances since the latter can provide chitosan-containing polysaccharides which never give out large quantities of disagreeable and offensive smells and, in particular, preferably used herein are fungi. Among fungi usable herein, preferred are *Agaricus bisporus, Lentinus edodes, Flammulina velutipes, Lyophyllum Karst (Lyophyllum shimeji or aggregatum), Grifola frondosa*, and *Pholiota nameko* and particularly preferably used herein are *Agaricus bisporus, Lentinus edodes, Flammulina velutipes* and *Lyophyllum Karst (Lyophyllum shimeji or aggregatum)*.

When using a fungus as a raw material, it may be fresh one or a dried product thereof, but it is common that the hard tip of the stem thereof is removed followed by washing with water to thus completely remove the extraneous matter such as mud. At this stage, unless the raw material is sufficiently washed, the impurities adhered thereto would remain even in the final product. The raw material is then pulverized or sliced, if necessary, by the use of a mixer or a slicing machine before the heat-treatment thereof in an aqueous caustic alkali solution having a high concentration and preferably in an aqueous caustic alkali solution having a concentration ranging from 25 to 50% by mass. Such caustic alkalis preferably used herein may be, for instance, caustic soda and caustic potash. Such an alkaline aqueous solution is preferably added to the raw material in an amount ranging from 40 to 50 parts by mass per 100 parts by mass (dry mass) of the raw material and then the raw material is preferably heat-treated at a temperature ranging from 90 to 120° C. for a time ranging from 0.2 to 30 hours and more preferably at a temperature ranging from 100 to 110° C. for a time ranging from 1 to 10 hours.

In this connection, the method of the present invention makes use of a concentrated aqueous caustic alkali solution and accordingly, it is preferred to use a reaction vessel made of, for instance, porcelain or hard glass. This heat-treatment may be carried out at ordinary pressure, at a reduced pressure or under pressure, but it is in general sufficient to carry out the heat-treatment at ordinary pressure.

Moreover, the raw material may likewise be subjected to a pre-treatment such as a treatment with an enzyme such as a cellulase, a glucanase and/or protease and/or a freezing-thawing treatment prior to the heat-treatment. The treatment with an enzyme is preferably carried out at a temperature ranging from 25 to 40° C. for 2 to 24 hours while using an enzyme solution obtained by adding the foregoing enzyme to water in a concentration ranging from 0.01 to 0.1% by mass. Cell walls or proteins present in the raw material used are hydrolyzed through this treatment with an enzyme and accordingly, the treatment makes the preparation of the desired chitosan-containing polysaccharide quite easy. Alternatively, if the raw material is first frozen and then thawed, the tissues (or cell walls) of the raw material are destroyed and accordingly, the desired chitosan-containing polysaccharide can likewise quite easily be prepared in this case. In particular, when the raw material is pre-treated by, for instance, a freezing-thawing treatment, a cutting treatment into small pieces using a slicing machine and/or a pulverization treatment using a mixer, the fibrous materials of the fungus used are disentangled and this may improve the efficiency of such an enzyme treatment (for instance, the treatment with a cellulase).

For instance, 10 kg of pre-treated fungus is suspended in 20 L of pure water, a cellulase is then added to the resulting suspension in an amount ranging from about 6 g to 60 g, the resulting mixture is heated to a temperature of 40° C. for 2 hours, then at 60° C. for 2 hours and the heat-treatment is further continued while raising the temperature thereof till the mixture starts boiling. Examples of the foregoing cellulase usable herein are that derived from *Aspergillus niger*, those derived from strains belonging to the genus *Bacillus* (alkaline cellulases), that derived from *Tricoderma reesei* and that derived from *Anthrobacter*.

The mixture is roughly cooled and then caustic soda or caustic potash is added thereto to a final concentration of about 50% by mass. At this stage, the temperature of the mixture increases to a level of not less than 100° C., but the heat-treatment is continued for about 2 to 4 hours at that temperature. After the completion of the heat-treatment, the reaction vessel is closed with a lid without subjecting it to any post-treatment and allowed to cool overnight. The reaction vessel should be closed so as to prevent the alkali from causing any deterioration through the absorption of carbon dioxide in the air. This heat-treatment would permit the deacetylation of the amino groups of chitin-containing polysaccharides to thus form chitosan-containing polysaccharides.

The layer of the chitosan-containing polysaccharide thus formed on the upper surface of the alkali-treated liquid is recovered by scooping the same with a wire netting (100 mesh). The further decantation would permit the recovery of the precipitates deposited on the bottom of the vessel. The remaining alkaline liquid can be reused in the subsequent alkali-treatment without any additional treatment.

The resulting mixture is subjected to a solid-liquid separation according to a means such as centrifugation, filtration and/or decantation. The resulting solid matter mainly comprises chitosan-containig polysaccharides. More specifically, the solid matter or the crude chitosan-containing polysaccharide is suspended in about 2 to 10 volumes of pure water, transferred to a bleached cotton fabric and sufficiently washed with pure water till the wash liquid becomes neutral. In this regard, it is quite important to use pure water. This is because the crude chitosan-containing polysaccharides obtained at this stage may have an ability to quite efficiently adsorb impurities such as metal ions present in, for instance, tap water. Moreover, the washing treatment should be conducted as soon as possible so as to prevent any excess increase of the viscosity and this would make the subsequent treating steps quite difficult. In this respect, it is effective to treat the processing liquid with an organic solvent such as ethanol if the viscosity of the same increases extremely. This treatment makes the subsequent filtration quite easy.

Then the crude chitosan-containing polysaccharides obtained after the water-washing is dissolved in an aqueous organic acid solution. Examples of such organic acid usable in this step are acetic acid, malic acid and ascorbic acid The concentration of the organic acid preferably ranges from 1 to 20% by mass and more preferably 5 to 10% by mass. The crude product is treated with the organic acid solution at a temperature ranging from 5 to 40° C. for 0.1 to 48 hours and it is usually sufficient that the mixture is allowed to stand overnight at room temperature, for the dissolution thereof. The chitosan-containing polysaccharides are polymers and accordingly, the complete dissolution would require a considerable time. The resulting solution containing the chitosan-containing polysaccharides dissolved therein is treated by centrifugation, filtration and/or decantation to thus remove impurities present therein. In this connection, the centrifugation is most preferred since the viscosity of the solution is very high and the filtration and decantation thereof would require a considerably long period of time.

To the resulting clear and transparent chitosan-containing polysaccharide solution, there is added an alcohol (such as ethanol or methanol), acetone, or a caustic alkali (such as caustic soda) solution to precipitate the chitosan-containing polysaccharides and to thus recover the same. For instance, caustic soda can be added to the chitosan-containing polysaccharide solution in an amount of 0.01 to 0.5 part by mass per 100 parts by mass of the solution to thus precipitate the chitosan-containing polysacchalirides. The precipitates thus formed are subjected to a solid-liquid separation treatment by, for instance, centrifugation to thus recover pure chitosan-containing polysaccharides. The ethanol precipitation technique permits the easy handling of the polysaccharide solution since this makes the filtration easier, but this technique requires the use of a large quantity of solvent. This treatment requires the use of ethanol in an amount of at least 2 to 3 times the volume of the chitosan-containing polysaccharide solution. In addition, the chitosan-containing polysaccharides prepared using an alcohol has a tendency of showing high deliquescence. Moreover, the use of acetone and methanol is not preferred as a solvent for the foregoing treatment when using the resulting chitosan in or as a food, a medicine and a cosmetic product.

Accordingly, preferably used in the usual solid-liquid separation step is an operation for precipitating the polysaccharides with an alkali. This processing step can be repeated to remove impurities, but it is rather preferred not to make the step undesirably complicated since the chitosan-containing polysaccharides have a high ability to adsorb impurities.

On the other hand, when it is intended to prepare a large quantity of chitosan-containing polysaccharides, it is quite dangerous to handle a large amount of a concentrated alkaline solution according to the centrifugation technique as a solid-liquid separation means and the centrifugation would be accompanied by considerable difficulties. In such case, it is desirable to use "a method free of any centrifugation" as will be detailed later.

More specifically, to a raw material such as mushroom which has been sufficiently washed and cut into slices having a thickness ranging from 1 to 3 mm, sliced *Lentinus edodes, Flammulina velutipes* cut into halves or dried *Agaricus bisporus* reconstituted with water, there is added, for instance, caustic soda to a final concentration ranging from 40 to 60% by mass, for instance, 50% by mass. A trace amount of distilled water can, if necessary, be added to each mixture for ensuring the complete dissolution of the alkali. Each resulting mixture is heated to a temperature ranging from 80 to 120° C. for 3 to 30 hours, for instance, at a temperature of not less than 110° C. for not less than 2 hours and then the mixture is allowed to cool. To each mixture, there is, if necessary, added distilled water in an amount of not less than the equivalent volume and preferably 3 to 4 times the volume of the mixture, or a solution of an inorganic acid (such as hydrochloric acid or sulfuric acid) or an organic acid (such as acetic acid, ascorbic acid or lactic acid) having a concentration ranging from 10 to 20% by mass to thus control the viscosity of each mixture to a level of 3 to 20 mPa·s and preferably 5 to 10 mPa·s. At this stage, each mixture is allowed to stand overnight and the pH value thereof is, if necessary, adjusted to the range of from 9 to 6.5 and preferably 7. Then the mixture is filtered through a filter such as that made of stainless steel, a bleached cotton fabric or a cheese cloth.

At this stage, if the viscosity of the mixture increases, this makes the subsequent filtration steps difficult and therefore, it would be important to devise the way how to add the distilled water and/or the inorganic/organic acid solution so as not to increase the viscosity of the mixture. To this end, it would be recommendable to conduct a preliminary test using a part of the sample or the mixture. The inorganic or organic acid is preferably added in such a manner that the pH value of the sample is adjusted to a level ranging from 9 to 6.5 and preferably 7.

The resulting solid matter is again suspended in distilled water and the pH value thereof is always maintained at a level ranging from 9 to 6.5 and preferably 7, while gently stirring the same. Again the suspension is filtered or decanted to remove the solvent and then distilled water is added. The foregoing operations are repeated till the salt concentration and pH value thereof are sufficiently reduced. Finally, the mixture is filtered through a cheese cloth, followed by the dehydration by the application of a pressure and the subsequent lyophilization of the solid matter thus obtained to thus give a dried product.

In the preparation of chitosan-containing polysaccharides from the resulting crude chitosan-containing polysaccharides, the currently used "method which makes use of the centrifugation technique" can be employed because of the small amount of the crude chitosan-containing polysaccharides to be handled and the low degree of alkalinity thereof. In other words, the crude chitosan-containing polysaccharides are dissolved in a 5 to 10% acetic acid solution and the resulting solution is sufficiently stirred before the centrifugal separation, the resulting supernatant is neutralized with an alkali, the neutralized supernatant is again centrifuged, followed by washing the resulting chitosan-containing fraction (precipitated portion) with water, the filtration thereof through a bleached cotton fabric or a cheese cloth, the compression of the chitosan-containing fraction for the reduction of moisture present therein and the lyophilization thereof to thus give purified chitosan-containing polysaccharides.

The chitosan content of the chitosan-containing polysaccharide according to the present invention may vary depending on the conditions for the preparation thereof selected, but it in general ranges from 5 to 80% by mass and, in particular, falls within the range of from 15 to 75% by mass.

The chitosan content of chitosan-containing polysaccharides can be determined according to the following method:

The powdery chitosan-containing polysaccharide (0.5 g) is accurately weighed out and then dissolved in a 5% by volume aqueous acetic acid solution in such a manner that the volume of the resulting solution is correctly equal to 100 g. This solution (1 g) is accurately weighed out into a 200 ml volume conical flask and 30 ml of de-ionized water is added to the flask, followed by sufficient stirring of the mixture. Two to three drops of a 0.1% Toluidine Blue solution are added to the mixture as an indicator and the content of chitosan present therein is determined by the titration of the mixture with an aqueous solution of N/400 potassium polyvinyl sulfate $[(C_2H_3OSK)_n$, wherein n=not less than 1500]. The degree of deacetylation (or the chitosan content=the content of glucosamine) can be determined according to the following relation:

$$\text{Deg. of Deacetylation} = (X/161)/[(X/161)+(Y/203)] \times 100(\%)$$

wherein $X=(1/400) \times (1/1000) \times f \times 161 \times \upsilon$; $Y=0.5 \times (1/1000)-X$; $\upsilon$=Titer (ml; titrated amount) of the aqueous solution of N/400 potassium polyvinyl sulfate; f=The factor of the aqueous solution of N/400 potassium polyvinyl sulfate.

The factor f is 1.005 in this case.

The foregoing equation can be converted into the following relation:

$$\text{Deg. of Deacetylation} = [203X/(203X+161Y)] \times 100(\%)$$

wherein $X=1.005 \times 161 \times \upsilon$ (titer; ml); and $Y=5-X$.

The purified chitosan-containing polysaccharide can, if necessary, again be dissolved in the foregoing dilute organic acid solution, for instance, a 1 to 5% aqueous acetic acid, malic acid or ascorbic acid solution, followed by repeating the foregoing neutralization-precipitation operations using an alkali to thus further purify the chitosan-containing polysaccharide. However, it is in general sufficient to carry out the neutralization-precipitation treatment only one time. The soluble and purified chitosan-containing polysaccharide in the form of a solution in a dilute organic acid solution can be spray-dried or lyophilized to thus recover the polysaccharide in the form of white powder. The soluble chitosan-containing polysaccharide can immediately or instantaneously be dissolved in pure water. The pure chitosan-containing polysaccharide obtained after the alkali-precipitation treatment is directly lyophilized. This product is insoluble in pure water and therefore, it can first be dissolved in a dilute organic acid solution, for instance, an aqueous acetic acid, malic acid or ascorbic acid solution prior to its practical use. This product is hardly soluble in a hydrochloric acid solution.

Medicine or Food Obtained Using Qhitosan-Containing Polysaccharides

The chitosan-containing polysaccharides according to the present invention have effects of lowering, for instance, the blood pressure, urine-sugar level, blood-sugar level, overall cholesterol level, uric acid level and neutral fat level. The chitosan-containing polysaccharides of the present invention accordingly would show considerable effects of improving various numerical values of inspection concerning various diseases originated from living habits such as hypertension and diabetes and geriatric diseases and they are thus suitably used as or in medicines and foods.

When using the chitosan-containing polysaccharides according to the present invention in the form of a liquid preparation, such a medicine or food is prepared by optionally incorporating, into the chitosan-containing polysaccharides, various additives, for instance, a preservative such as sodium benzoate, methyl p-oxybenzoate or sodium dehydroacetate; a solubilizing agent such as malic acid, ascorbic acid, citric acid or acetic acid; a coloring agent; a perfume; a flavor; and a sweetening agent such as glucose or mannitol and further optionally adding a diluent such as distilled water or physiological saline.

The medicine containing the chitosan-containing polysaccharide as an effective component is usually prepared in any solid dosage form such as a tablet, a pill, a powder, a granule, a capsule or a suppository. In the preparation thereof, these pharmaceutical preparations are prepared using any currently used diluent or excipient such as a filler, a thickener, a binder, a humectant, a disintegrator, a surfactant and/or a lubricant.

When they are prepared in the form of a tablet, a carrier may be one which has conventionally and widely been used in this field and specific examples thereof are an excipient such as crystalline cellulose, lactose, mannitol, sucrose, sodium chloride, glucose, starch, calcium carbonate, kaolin; a binder such as polyvinyl pyrrolidone, distilled water, physiological saline, simple syrup, glucose injection, starch solution, gelatin solution, carboxymethyl cellulose, potassium phosphate; a disintegrator such as lactose, dry starch, sodium alginate, agar powder, sodium hydrogen carbonate, calcium carbonate, sodium lauryl sulfate, stearic acid monoglyceride, starch; a disintegration-inhibitory agent such as hydrogenated oils, sucrose, stearin, cacao butter; a dissolution/absorption promoting agent such as malic acid, acetic acid, ascorbic acid; an adsorbing agent such as colloidal silicate, glycerin, starch, lactose, kaolin, bentonite; and a lubricant such as polyethylene glycol, purified talc, stearic acid salts. The tablet may, if necessary, likewise be formed into a sugar-coated tablet, a gelatin-coated tablet, an enteric coated tablet, a film-coated tablet, or a double layer tablet or a multilayer tablet.

When the pharmaceutical preparation is formed into a pill, a carrier may be one which has conventionally and widely been used in this field and specifc examples thereof are an excipient such as glucose, lactose, mannitol, starch, cacao butter, hardened (hydrogenated) plant's oil, kaolin, talc; and a disintegrator such as powdered gum Arabic and gelatin. When the pharmaceutical preparation is prepared in the form of a suppository, a carrier may be one which has conventionally and widely been used in this field and specific examples thereof are cacao butter, esters of higher alcohols and gelatin.

The amount of the chitosan-containing polysaccharide used as an effective component is not restricted to any specific range and may widely vary, but the polysaccharide is in general used in an amount ranging from 1 to 90% by mass and preferably 10 to 70% by mass.

The dose thereof is not particularly limited and appropriately selected while taking into consideration various conditions such as the direction for use, the age and the sex of each particular patient, and the extent of each particular disease and the dose of the chitosan-containing polysaccharide in general ranges from 0.1 to 10 mg and preferably 0.5 to 5 mg per unit body weight (1 kg) per day and it is orally administered while dividing the same into 1 to 4 portions. In this respect, if the content of the chitosan-containing polysaccharide is high, the use thereof may cause vitamin deficiency diseases and hypoferremia or sideropenia since the polysaccharide may absorb or form a clathrate compound with iron or a vitamin, but the dose falling within the range specified above has a relatively low content of the polysaccharide and therefore, it is not necessary to supplement iron-containing component and vitamins.

The chitosan-containing polysaccharide of the present invention may be incorporated into any food and specific examples thereof are soup, miso soup, drinks, jelly and gumi. The content of the chitosan-containing polysaccharide in these foods preferably ranges from 0.01 to 5.0% by more preferably 0.02 to 1.0% by mass and most preferably 0.05 to 0.5% by mass.

EXAMPLES

The method for preparing the chitosan-containing polysaccharide of the present invention and biochemical characteristics of the chitosan-containing polysaccharide will hereunder be described in more detail with reference to the following Examples.

Preparation Example 1

Preparation of Chitin Derived from Fungi

The hard tips of *Agaricus bisporus* soiled with mud were cut off and as a result of weighing, the mass of the raw material was found to be 440 g. To the raw material, there was added 900 ml of a solution containing 1% malic acid and 0.1% ascorbic acid and the resulting mixture was twice blended for 30 seconds in a mixer. The temperature of the mixture was maintained by dipping the same in water bath (100° C.) for 120 minutes with occasional stirring. Thus, the temperature of the suspension was raised up to about 70 to 85° C. Then the suspension was slowly filtered by suction over 2 to 3 hours The residue remaining on the filter paper was scraped out from the paper with a spatula and the rest thereof was recovered while rinsing the paper with pure water. Thus a crude chitin-containing suspension was obtained in an amount of about 600 ml (as expressed in terms of the volume thereof). To this suspension, there was added 600 ml of an N—NaOH solution, followed by heating in a water bath at 60° C. for 20 minutes and the subsequent suction filtration. The resulting filter cake was washed with pure water and then ethanol.

The crude chitin-containing polysaccharide remaining on the filter paper was suspended in 1000 ml of pure water, the resulting suspension containing chitin-containing polysaccharide derived from the fungus (fungal chitin-containing polysaccharide) was neutralized with an N—HCl solution and then centrifuged at 4500 rpm. The fungal chitin-containing polysaccharide-containing fraction included in the resulting precipitates was suspended in 99% ethanol to thus give about 1000 ml of a suspension. Then the suspension was filtered through two sheets of filter paper put on top of each other. The filter cake was washed with about 500 ml of ethanol and then it was completely aspirated. The amount of the purified chitin-containing polysaccharide fraction was found to be about 53 g in its wet condition. This fraction was put in a desiccator the bottom of which had been covered with silica gel and then dried under a reduced pressure to thus give 5.54 g of purified chitin-containing polysaccharides.

The yield of dried and purified chitin-containing polysaccharides was thus found to be 1.260 g per 100 g of the fresh *Agaricus bisporus*. At this stage, the dried chitin-containing polysaccharide thus obtained was in a rice cracker-like shape and it could easily be loosened and divided with a pincette.

Preparation Example 2

Preparation of Chitosan-Containing Polysaccharide from Fungal Chitin-Containing Polysaccharide To 4.99 g of the dried and purified chitin-containing polysaccharide derived from *Agaricus bisporus* prepared in Preparation Example 1, there was added 200 ml of a 50% aqueous solution of NaOH to thus give a suspension. The resulting suspension was heated to 90° C. for 2 hours with occasional stirring. Then it was centrifuged (at 4500 rpm, for 15 minutes at 4° C.; all the centrifugation operations in the following operations and in the subsequent Examples will likewise be conducted under the same conditions used herein) to thus recover the solid matter. The principal components of this solid matter are chitosan-containing polysaccharides.

To the solid matter, there was added 1000 ml of a 10% aqueous acetic acid solution, the resulting mixture was homogenized, allowed to stand overnight without conducting any particular treatment to thus ensure the dissolution of the chitosan-containing polysaccharides. The resulting solution was found to be highly viscous. The solution was again centrifuged to recover the supernatant. The precipitated fraction was again dissolved in a 10% aqueous acetic acid solution to extract the chitosan-containing polysaccharides and the extract was added to the supernatant. The pH value of the combined supernatant was controlled to 10. The supernatant was centrifuged, 1000 ml of pure water was added to the resulting precipitated fraction and the mixture was then centrifuged, followed by the repetition of these operations three times. The pH value was found to be 10 after the first washing, 7.5 observed after the second washing and finally about 6.5 after the third washing operation.

The precipitates were transferred to a sheet of filter paper and dried under a reduced pressure at 25° C. for 40 hours.

Thus, chitosan-containing polysaccharides having a glucosamine content of 55% was obtained in an overall amount of 1050 mg.

The yield of the chitosan-containing polysaccharides was found to be 210 mg per 1 g of the starting chitin-containing polysaccharides.

The chitosan-containing polysaccharides were hydrolyzed under the following conditions, the resulting hydrolyzate was analyzed by the thin layer chromatography technique carried out under the following conditions and as a result, glucosamine and glucose were detected in a ratio of about 3:1. Any monosaccharide other than those described above and any galactosamine were not detected at all. The glucosamine content as determined by the thin layer chromatography was found to be higher than that determined by the polyvinyl sulfate technique, but the reason of this would possibly be such that the amount of glucose produced was smaller than that of glucosamine under the hydrolysis conducted at 100° C. in a 4M-HCl or that the hydrolysis further proceeded.

Conditions for the Hydrolysis of Chitosan-Containing Polysaccharides:
Medium: 4M-HCl solution; Temperature: 100° C.; Duration: 3 hours Conditions for Thin Layer Chromatography of Hydrolyzate:
Carrier: Whatman 4860-820 (thickness: 250 µm);
Developing Solvent: n-butanol/pyridine/0.1M-HCl solution (5:3:2);
Development: This was carried out at room temperature for 2 hours;
Color Developing Agent: Diphenylanine/aniline/phosphoric acid Preparation Example 3

Preparation of Chitosan-Containing Polysaccharides from Sliced *Agaricus bisporus*

The hard tips of *Agaricus bisporus* soiled with mud were cut off and as a result of weighing, the mass of the raw material was found to be 546 g. The raw material was sliced into thin pieces having a thickness of about 1 mm using a kitchen knife or a food processor. To the raw material, there was added 900 ml of a solution containing 1% malic acid and 0.1% ascorbic acid and the resulting mixture was twice blended for 30 seconds in a mixer. To each of two 1000 ml volume beakers, there were added 270 g each of the sliced raw material thus prepared and 270 g each of solid NaOH. After allowing each mixture to stand for about 15 minutes, the sliced *Agaricus bisporus* was compatible with the alkali and the volume of each mixture was reduced. The contents of these two beakers were combined and then heated in a water bath. The mixture was heated to a temperature ranging from 90 to 95° C. for about 2 hours with stirring and then allowed to cool down to room temperature.

The floating fungal bodies principal component thereof was chitosan-containing polysaccharide) were carefully scooped up with a spoon for removing lye, followed by rinsing the same three times with 80% ethanol. More specifically, the fungal bodies thus recovered were washed with 600 to 800 ml each of ethanol for 10 minutes while gently stirring the mixture. Further, they were washed twice with 1000 ml of pure water, followed by the addition of 25 ml of acetic acid, confirmation of whether the wash liquid had a neutral pH value or not, the addition of 1/10 volume of acetic acid and allowing the mixture to stand overnight to thus ensure the dissolution of chitosan-containing polysaccharides present therein. The resulting mixture was filtered through a cheese cloth, the filtrate was neutralized with a 50% NaOH solution to thus precipitate the chitosan-containing polysaccharides.

The precipitates thus obtained were separated by centrifugation, dissolved in acetic acid solution and stored at 4° C. over 64 hours to ensure the complete dissolution of chitosan-containing polysaccharides. This acetic acid solution of chitosan-containing polysaccharides (600 ml of a 10% acetic acid solution) was centrifuged to recover the resulting supernatant (pH 4.48). The precipitated fraction was again extracted with 500 ml of a 10% acetic acid solution (pH 2.18) and the resulting supernatant was recovered and combined with one previously recovered. The combined supernatant was neutralized (pH 10), and the precipitates of chitosan-containing polysaccharides thus formed were recovered through centrifugation. The precipitates were dissolved in 500 ml of a 10% acetic acid solution and the resulting solution was centrifuged to recover the supernatant. To the supernatant, there was again added a 50% NaOH solution to neutralize the same and the precipitates formed were recovered by centrifugation.

To the precipitates, there was added 500 ml of water to form a suspension and then the suspension was centrifuged. These operations were repeated twice. After the completion of these operations, brown precipitates were formed. The precipitates were lyophilized. In this case, the precipitates were frozen using a dry ice/acetone mixture. The yield of the precipitates attained after the lyophilization was found to be 2702 mg. In this respect, the content of glucosamine in the chitosan-containing polysaccharides was found to be 19.6% and this corresponded to the yield of the chitosan-containing polysaccharides of 495 mg per 100 g of the starting fresh fungus.

Preparation Examples 4 and 5

Effect of Autoclave-Treatment and Added Malic Acid

The hard tips of fresh *Agaricus bisporus* were removed, the resulting fungal bodies were washed with water and they were pulverized for 30 seconds in a mixer. The pulverized fungal bodies were divided into two portions, 200 ml of pure water was added to one portion thereof, while 200 ml of a 5% aqueous malic acid solution was added to the other portion, each mixture was treated at 120° C. for 30 minutes in an autoclave and then allowed to stand over a whole day and night. Each mixture was filtered through a gauze and then suspended in pure water to thus give each suspension having a final volume of 200 ml.

To each suspension, there was added 200 g of NaOH and each mixture was heated at 120° C. for 30 minutes in an autoclave. Thereafter, about 200 ml of pure water was added to each suspension and then centrifuged. The precipitates of chitosan-containing polysaccharides were recovered and then dissolved in a 10% acetic acid solution. The solution was centrifuged to obtain a supernatant, followed by the neutralization of the latter with a 25% NaOH solution and the subsequent centrifugation to thus recover the precipitates of chitosan-containing polysaccharides formed. The resulting precipitates of chitosan-containing polysaccharides were additionally washed three times with 500 ml each of pure water according to the centrifugation. After these three times of washing operations with pure water, the pH value was reduced to a level of about 7.5.

Thereafter, the resulting precipitates were lyophilized and then inspected for the yields and glucosamine contents. As a result, the yields were found to be 643 mg and 713 mg respectively, while the glucosamine contents were found to be 71.3% and 37.6%, respectively.

In this connection, it was found that the highest glucosamine content was observed when the raw material was treated with pure water and then treated in an autoclave.

Preparation Example 6

Preparation of Chitosan-Containing Polysaccharides While Making Use of Pre-treatment with Cellulase In this Preparation Example, fresh *Agaricus bisporus* as a raw material was treated with a cellulase and then heat-treated in the coexistence of a concentrated alkali to thus obtain chitosan-containing polysaccharides soluble in a dilute organic acid solution and insoluble in an alkaline solution. Then the polysaccharides were lyophilized to give about 11 g of a powdery product. These procedures were detailed below.

*Agaricus bisporus* (3.2 kg) was quickly washed with water to thus completely remove the mud or soil attached thereto. Then the raw material was sliced into small pieces having a thickness of 1 mm. These slices were suspended in 5600 ml of pure water, 12 g of a cellulase (cellulase originated from *Aspergillus niger*; the product used for foods) was added to the suspension, the resulting mixture was heated to 40° C. for 2 hours and 60° C. for 2 hours and then the temperature was further raised till the suspension started boiling.

The suspension was roughly cooled and then caustic soda was added thereto to a final concentration of about 50%. At this stage, the temperature of the suspension increases to a 110° C., but the heat-treatment was further continued for about 3 hours at that temperature. After the completion of the heat-treatment, the reaction vessel was closed with a lid without subjecting it to any post-treatment and allowed to stand over 3 days. The layer of the chitosan-containing polysaccharide thus formed on the upper surface of the alkali-treated liquid was recovered by scooping the same with a wire netting (100 mesh) of stainless steel. The precipitates of the chitosan-containing polysaccharide which were formed and deposited on the bottom of the vessel were likewise recovered through decantation.

The resulting crude chitosan-containing polysaccharide (15 g) was suspended in about 300 volumes of pure water, transferred to a bleached cotton fabric and sufficiently washed with pure water till the wash liquid became neutral. Then the crude chitosan-containing polysaccharides obtained after the water-washing were slowly dissolved in a 10% aqueous acetic acid solution over one to two hours. The resulting solution containing the chitosan-containing polysaccharides dissolved therein was treated by centrifugation to thus remove impurities present therein. To 3500 ml of the resulting clear and transparent solution of chitosan-containing polysaccharides, there was added about 500 ml of a 10N—NaOH solution to thus precipitate and recover the chitosan-containing polysaccharides. The precipitates thus recovered were washed with 3 L of pure water and then centrifuged The resulting purified chitosan-containing polysaccharides were lyophilized to thus give 10.8 g of off-white powdery product.

The following Table 1 shows the results obtained in the foregoing Preparation Examples 2 to 6 in which chitosan-containing polysaccharides (abbreviated as "Chit. Cont. PolySA.") were prepared:

TABLE 1

| Sample of Chit. Cont. PolySA. | Wt. of raw material | Dry Wt. of Chit. Cont. PolySA. | Content of Glucosamine (%)[1] | Remarks |
|---|---|---|---|---|
| Preparation Ex. 2 | 440 g | 1050 mg | 55.5 | Pulverized in a Mixer. |
| Preparation Ex. 3 | 546 g | 2702 mg | 19.6 | Using sliced fungus. |
| Preparation Ex. 4 | 200 g | 643 mg | 71.3 | Autoclave-Treatment |
| Preparation Ex. 5 | 200 g | 713 mg | 37.6 | Autoclave-Treatment |
| Preparation Ex. 6 | 3.2 kg | 10.8 g | 64.1 | Using a cellulase |
| Cuticle of king crab | 8 g* | 801 mg | 82 | *corresponding to 1 g of chitin |
| Cuticle of prawn | 16 g* | 781 mg | 85 | *corresponding to 1 g of chitin |

[1]As will be detailed below, it would be recognized that this measured value of "Content of glucosamine" may reflect the content of chitosan per se in case of the chitosan-containing polysaccharide.

Preparation Example 7

Method for Preparing "Crude Chitosan-Containing Polysaccharides" Without Using any Centrifugation To a mixture containing 120 kg (as expressed in terms of the mass of fresh fungi) each of mushroom which had been sufficiently washed and cut into slices having a thickness ranging from 1 to 3 mm, sliced *Lentinus edodes*, *Flammulina velutipes* cut into halves and dried *Agaricus bisporus* reconstituted with water, there was added about 500 kg of NaOH to a final concentration of 50%. In this respect, 100 kg of distilled water was added to the mixture so that NaOH could sufficiently be dissolved. The mixture was heated to a temperature ranging from 90 to 110° C. for not less than 2 hours and then allowed to cool overnight. to the mixture, there was added 5 volumes of a 20% by mass citric acid solution and the resulting mixture was allowed to stand overnight without any post-treatment. The pH value of the mixture was found to be 8.0 at this stage. On the next day, the mixture was filtered through a filter of a cheese cloth.

The solid matter formed was again suspended in 1000 L of distilled water and the pH thereof was controlled such that it was always maintained at 7 while gently stirring the suspension. Again, the suspension was filtered and distilled water was added. These washing operations were repeated three times till the salt concentration and the pH value were sufficiently lowered. Finally, the suspension was filtered through a cheese cloth, dehydrated by applying a pressure and the resulting solid matter was lyophilized to thus give about 5.6 kg of a dry product. The recovery of the crude chitosan-containing polysaccharides was found to be 1.2% on the basis of the mass of the raw material which was assumed to be 480 kg.

The crude chitosan-containing polysaccharides (5.6 kg) were dissolved in 100 L of a 10% by mass aqueous acetic acid solution, the mixture was centrifuged after sufficient stirring thereof, the resulting supernatant was neutralized and then centrifuged to give a chitosan-containing fraction or precipitates were washed with water, followed by the filtration thereof through a cheese cloth, the reduction of moisture included in the filter cake by the application of a pressure and the subsequent lyophilization to thus give 1.2 kg of chitosan-containing polysaccharides.

The recovery of the chitosan-containing polysaccharides was found to be 0.25% with respect to the amount of the raw material and this clearly indicates that the chitosan-containing polysaccharides are contained in the crude chitosan-containing polysaccharides in an amount of not less than 20%.

Preparation Example 8

The same procedures used in Preparation Example 7 were repeated except that after the heat-treatment under the alkaline conditions, 2000 L of a 20% by mass lactic acid solution was added in place of the 5 volumes of a 20% by mass citric acid solution used in Preparation Example 7 and the resulting mixture was allowed to stand overnight without carrying out any particular treatment. As a result, it was found that results almost identical to those observed in Preparation Example 7 were obtained.

Preparation Example 9

The same procedures used in Preparation Example 7 were repeated except that after the heat-treatment under the alkaline conditions, 2000 L of a 20% by mass acetic acid solution was added in place of the 5 volumes of a 20% by mass citric acid solution used in Preparation Example 7 and the resulting mixture was allowed to stand overnight without carrying out any particular treatment. As a result, it was found that results almost identical to those observed in Preparation Example 7 were obtained.

Example of Pharmaceutical Preparation 1

Tablet Containing Chitosan-Containing Polysaccharide

To 10 g of the chitosan-containing polysaccharide prepared in Preparation Example 6, there were added 10 g of malic acid and 10 g of ascorbic acid, followed by the dissolution of the polysaccharides in 1000 ml of water and the subsequent lyophilization to thus give water-soluble chitosan. This product has such characteristic properties that it can immediately be dissolved in pure water. To 10 g of this lyophilized product, there were added 20 g of mannitol, 50 g of lactose, and 20 g of polydextrose, they were then sufficiently admixed and 2 g of a sucrose ester of fatty acid was added as a binder to thus form a tablet.

The resulting tablet has effects of lowering, for instance, the blood pressure, urine-sugar level, blood-sugar level, uric acid level, overall cholesterol level and neutral fat level in patients suffering from various diseases originated from living habits such as hypertension and diabetes and geriatric diseases.

Example 1

Analysis of Components Present in Purified Chitosan-Containing Polysaccharides

The chitosan-containing polysaccharide prepared in Preparation Example 6 was inspected for the following properties according to the methods detailed below:

The chitosan-containing polysaccharide was inspected for the presence of proteins and reducing polysaccharides according to the biuret reaction and the anthrone-sulfuric acid reaction respectively, but both of them were not detected at all.

The chitosan-containing polysaccharide was found to be negative to the iodo-starch reaction, but it was slightly colored in brown, which was peculiar to chitosan.

The glucosamine content of the chitosan-containig polysacchaxide was determined according to the polyvinyl-sulfuric acid reaction and the Elson-Morgan reaction. Almost the same results were obtained in these methods.

The chitosan-containing polysaccharide was inspected for the presence of $\beta(1\rightarrow3)$, but it was found to be lower than the detection limit.

In this connection, however, the chitosan-containing polysaccharide prepared according to the procedures used in Preparation Example 6 except for using ethanol instead of caustic soda shows considerable deliquescence and hygroscopic property.

When the raw material is pulverized by a mixer as in Preparation Example 1, the polysaccharide moiety may be physically decomposed or broken into short saccharides and therefore, the content of chitosan moiety increases, while when it is sliced as in Preparation Example 3, the polysaccharide moiety still remains therein in a large quantity and these operations may provide chitosan-containing polysaccharides quite similar to naturally-occurring ones (in other words, the content of chitosan moieties is high).

Example 2

Chitosan-Containing Polysaccharides Present in Fungi Frequently Observed in the Market Chitosan-containing polysaccharides were prepared by treating a variety of fungi generally observed in the market according to the same procedures used in Preparation Example 2. The following Table 2 shows the content (mg) of the chitosan-containing polysaccharide present in each fungus per 100 g of the corresponding fresh fungus, the glucosamine content (% by mass) in each chitosan-containing polysaccharide and the molecular weight of each chitosan-containing polysaccharide. The molecular weight of each polysaccharide was determined by dissolving each polysaccharide in a 5% aqueous acetic acid solution, allowing the solution to stand for a whole day and night (each chitosan-containing polysaccharide concentration: 0.05%) and determining the viscosity of each solution using an Ostwald viscometer (SHIBATA 2630-1). In this respect, each molecular weight was calculated according to the following relation:

$$\mathrm{Log}\ M = (\log(C \times \ln(\eta_{rel})) + 3.05/0.71$$

wherein [$\eta_{rel}$] represents each relative viscosity as determined from the foregoing experimental results of the viscosity measurement.

TABLE 2

| Raw Material | Content of chitosan-containing polysaccharide (mg) (Note 2) | Content of glucosamine (%) | Molecular weight of chitosan-containing polysaccharide ($\times 10^{-4}$) |
|---|---|---|---|
| Lyophyllum shimeji | 86 | 24 | 15.8 |
| Lentinus edodes | 217 | 26 | 12.3 |
| Flammulina velutipes | 496 | 15 | 12.9 |
| Agaricus bisporus | 239 | 51 | 39.8 |
| Grifola frondosa | 19 | 26 | 19.5 |
| Pholiota nameko | 5.2 | — | 1.70 |
| King Crab | About 10 g | 76 | |

(Note 2):
Each fungus is fresh one and contains about 90% of moisture. When using dried raw materials, they can provide chitosan in an amount of 10 times that listed above. Only small amounts of chitosan-containing polysaccharides were prepared from Grifola frondosa and Pholiota nameko.

This is because they have, by nature, quite low contents of chitin components. The results of the foregoing experiments clearly indicate that *Flammulina velutipes, Agaxicus bisporus* and *Lentinus edodes* can preferably be used in the present invention as raw materials for the chitosan-containing polysaccharides according to the invention since they are relatively cheap and easily available.

Example 3

Analysis of Components of Chitosan-Containing Polysaccharides

Each of the chitosan-containing polysaccharide prepared in Preparation Example 3 and commercially available crab chitosan was hydrolyzed by heating it in a 4M-HCl solution at 100° C. for 3 hours. Each hydrolyzate was developed according to silica gel (Whatman) thin layer chromatography: In this respect, the developing solvent used was a butanol/propanol/hydrochloric acid mixture and saccharides were colored using aniline reagent (see, for instance, M. Ghebregzabher, S. Rufini, G. M. Sapia & M. Lato, J. Chromatography, 1979, 180:1; and G. Zweig and J. Sherma (eds.), 1972; CRC Handbook of Chromatography, Vol. 1).

As controls, there were used glucose, galactose, galactosamine, glucosamine and N-acetyl glucosamine and the acid hydrolyzates of the chitosan-containing polysaccharide of the invention and the crab chitosan were simultaneously developed.

There were observed spots of glucosamine and the dimmer thereof for the acid hydrolyzate of the crab chitosan, while the acid hydrolyzate of the chitosan-containing polysaccharide showed a spot of glucose in addition to the same spots of glucosamine and the dimmer thereof observed for the crab chitosan. The amount of the glucosamine dimmer was found to be about 10% of the glucosamine monomer for both of the acid hydrolyzate of the crab chitosan and that of the chitosan-containing polysaccharide.

The chitosan-containing polysaccharide prepared in Preparation Example 3 is highly sensitive to the Molisch's reaction as compared with the chitosan-containing polysaccharide prepared in Preparation Example 2. This result is in good agreement with the data concerning the glucosamine contents.

Moreover, the hydrolyzate did not contain a disaccharide consisting of glucosamine and glucose and accordingly, it was proved that the chitosan-containing polysaccharide was completely free of any chimeric structure of glucosamine and glucose or it contained the same, if any, in an extremely small amount. Moreover, it would be predicted that such a chimeric structure is formed through quite complicated biosynthesis processes and it would accordingly be assumed that such a structure may be present in only a quite low probability.

The chitosan moiety of the chitosan-containing polysaccharide is a homopolymer of glucosamine and this moiety would govern the physical properties of the polysaccharide. In other words, even if the chitosan-containing polysaccharide has a glucosamine homopolymer content of only several percentages on the basis of the whole polysaccharide, the polysaccharide shows such characteristic properties required for the definition of the chitosan that it should be soluble in a dilute organic acid solution and insoluble in an alkaline solution, like the chitosan derived from the crustaceans. It would be recognized that the glucan portions of the chitosan-containing polysaccharide has a high hydrophilicity and the chitosan moiety is thus responsibly for the solubility in a dilute organic acid solution.

Example 4

Molecular Weight and Absorption Spectra of Chitosan-Containing Polysaccharide

The molecular weights of the chitosan-containing polysaccharides prepared in Preparation Examples 3 and 6 may in general vary depending on the conditions for the determination thereof. However, the following results were obtained.

In this connection, each measurement was repeated twice using an Ostwald's viscometer.

TABLE 3

| | Molecular Weight of Polysaccharides | | |
|---|---|---|---|
| Method of Determination | Preparation Ex. 3 | Preparation Ex. 6 | Crab Chitosan |
| Gel Filtration Chromatography | — | About 15($\times 10^{-4}$) | 40($\times 10^{-4}$) |
| Ostwald's viscometer | 6 to 13($\times 10^{-4}$) | 14 to 28($\times 10^{-4}$) | 40 to 58($\times 10^{-4}$) |

In the gel filtration chromatography, the gel carrier used was Cellulofine GCL 200m (trade name of a product available from Seikagaku Kogyo Company Ltd.) and the solvent used was a 10% acetic acid solution. As the molecular markers, there were used ferritin (44$\times 10^4$), $\gamma$-globulin (16$\times 10^4$), hemoglobin (6.45$\times 10^4$), egg white albumin (4.6$\times 10^4$) and cytochrome C. The molecular weight of the chitosan-containing polysaccharide prepared in Preparation Example 6 did not provide a single peak, it was dispersed in the range of from 5 to 40 ($\times 10^{-4}$) and the median of the molecular weight thereof was found to be about 15 ($\times 10^{31\ 4}$). That of the crab chitosan was dispersed in the range of from 2 to 100 ($\times 10^{-4}$) and the median of the molecular weight thereof was found to be about 40 ($\times 10_{-4}$).

On the other hand, when determixning the molecular weight using an Ostwald's viscometer and a mixture of 0.2M acetic acid solution/01M NaCl/4M urea solution as a solvent, the molecular weights were found to be 6 to 13 ($\times 10^{-4}$) for the chitosan-containing polysaccharide prepared in Preparation Example 3, 14 to 28($\times 10^{-4}$) for the chitosan-containing polysaccharide prepared in Preparation Example 6 and 40 to 58($\times 10^{-4}$) for the crab chitosan. In this connection, each molecular weight was calculated according to the relation of Mark-Houwink-Sakurada: $[\eta]=K \cdot M^a$. In the relation, $[\eta]$ represents the experimentally determined intrinsic viscosity and the constant values K and a were herein assumed to be $8.93 \times 10^{-4}$ and 0.71 respectively.

In addition, a solution of the chitosan-containing polysaccharide prepared in Preparation Example 2 in a 5% acetic acid solution (concentration: 2 mg/ml) was inspected for the ultraviolet-visible light absorbance. As a result, there was observed a small peak at wavelength ranging from 236 to 239 nm.

The chitosan-containing polysaccharide of the present invention was found to have a molecular weight as determined using an Ostwald's viscometer ranging from about 5 to about 40 ($\times 10^{-4}$).

The foregoing results suggest that the glucan moiety of the chitosan-containing polysaccharide of the present invention is a homopolymer of glucan having a complicated and branched structure. Moreover, it would likewise be presumed that the glucan moiety has a structure similar to those of glycogen and amylopectin, rich in β(1-6) branches, while taking into consideration, for instance, the following facts: the glucan moiety was highly hydrophilic; β(1-3) glucan was not detected at all; and the glucan moiety was not hydrolyzed with a cellulase.

Example 5

Test for Examining Taste and Palatability of Chitosan-Containing Polysaccharide

Ten persons (5 persons each of men and women) were requested to eat the chitosan-containing polysaccharide of the invention prepared in Preparation Example 3 and the commercially available crab chitosan (50 mg each). All of the panelists evaluated these substances as follows: The crab chitosan had unpleasant harshness, while the chitosan-containing polysaccharide of the invention had good taste and texture and was completely free of any disagreeable taste. This clearly suggests that the chitosan-containing polysaccharide of the invention never adversely affect the palatability and taste of any food which contains the polysaccharide incorporated into the same.

Example 6

Improving Effect of Chitosan-Containing Polysaccharide on Medical Examination Values The chitosan-containing polysaccharide-containing pharmaceutical preparation prepared in "Example of Preparation Example 1" was administered (100 mg/day) to a person (54-year-old) through the oral route over 6 months to thus evaluate the effects of improving various physiological values to be examined. The following Table 4 shows the results (changes of various physiological values observed in the person (54-year-old) before and after the oral administration of the chitosan-containing polysaccharide.

TABLE 4

| Items to be Examined | Bef. Adm. | Aft. Adm. | Std. value (Ref. value) |
| --- | --- | --- | --- |
| Body Wt. (kg) | | | |
| Blood Pressure | Max. 120 | Max. 98 | 90–139 |
| | Min. 80 | Min. 64 | 50–89 |
| Sugar in urine | 3(+) | 1(−) | 1(−) |
| Proteins in urine | 1(−) | 1(−) | 1(−) |
| Total cholesterol | 160 | 141 | 120–149 |
| Neutral fat | 71 | 60 | 30–149 |
| Uric acid level | 7.7 | 6.5 | 4.0–7.5 |
| Creatinine level | 0.7 | 0.8 | 0.7–1.2 |
| Uric acid nitrogen level | 12.9 | 11.8 | 8–21.9 |
| Occasional blood sugar (2 hrs. aft. a meal) | 145 | 112 | 70–110 |

The oral administration of the pharmaceutical preparation of the chitosan-containing polysaccharide according to the present invention over a long period of time (6 months) permitted the improvement of interested items such as the sugar level in urine, blood sugar level and uric acid level and the numerical values of these items were reduced to the normal levels. The pharmaceutical preparation likewise showed considerably high effects of lowering the total cholesterol level, the neutral fat level and the blood pressure.

There was not observed any change of the living attitude, environment and body weight in the panelist throughout the entire test term, while there were observed improvement in the medical examination values and accordingly, it would be said that the chitosan-containing polysaccharide of the present invention has considerable effects of improving the physiological values for diagnosing various diseases originated from living habits such as hypertension and diabetes and geriatric diseases.

INDUSTRIAL APPLICABILITY

The application of the technique for the production of the chitosan-containing polysaccharide according to the present invention would permit the production of novel chitosan-containing polysaccharides derived from vegetable raw materials starting from chitin-containing industrial wastes which have conventionally been disposed in a large quantity, for instance, solid contents of microorganisms such as beer yeast *Actinomycetes* obtained after the production of antibiotics; extracts from fungi; residues of a variety of fruits and/or vegetables; or seed coats of cereals. The resulting vegetable chitosan-containing polysaccharides can be expected as medicines as well as functional foods such as health foods. In this respect, however, these industrial wastes derived from beer- or ethanol-producing plants contain a large amount of amino acids, nucleic acids, proteins or the like and these components make it difficult or complicated to purify the intended chitosan-containing polysaccharides. For this reason, they are not directly used as raw materials for preparing chitosan-containing polysaccharides, but have practically been used as composts for use as beds for cultivating fungi and therefore, it would be desirable that they are regenerated in the form of fungi and then the chitosan-containing polysaccharides are produced from the fungi thus regenerated. This is because the latter method would permit the easy production of vegetable chitosan-containing polysaccharides having a high purity.

The method for the preparation of chitosan-containing polysaccharides according to the present invention can fundamentally be applied to all of the cereals and vegetable components containing chitin and accordingly, the method has very high usefulness.

What is claimed is:

1. A chitosan-containing polysaccharide characterized in having each of characteristics (a)–(h):
   (a) Constituent Saccharides of said polysaccharide consisting essentially of glucosamine and glucose in a molar ratio of from 1:5 to 5:1;
   (b) Molecular Weight of said polysaccharide of from about 50,000 to about 400,000;
   (c) Structural Units of said polysaccharide consisting essentially of chitosan moieties and glucan moieties;
   (d) Linkages of said polysaccharide comprising β(1→4) bonds and β(1→6) bonds but not comprising β(1→3) bonds;
   (e) Hydrolyzation with enzyme: the polysaccharide is not hydrolyzed with a cellulase, but is hydrolyzed into oligosaccharides by the action of a chitosanase;
   (f) Absence of Proteins and Reducing Polysaccharides in said polysaccharide;
   (g) Color of said polysaccharide being colorless;
   (h) Said polysaccharide being soluble in an aqueous acetic acid, malic acid or ascorbic acid solution having a concentration ranging from 5 to 10% by mass; said polysaccharide being insoluble in water, ethanol and an alkaline aqueous solution having a pH value of not less than 10.

2. The chitosan-containing polysaccharide of claim 1, wherein the molar ratio of glucosamine and glucose is 1:1.

3. The chitosan-containing polysaccharide of claim 1 or 2, wherein said polysaccharide has a chitosan content ranging from 18 to 72%.

4. The chitosan-containing polysaccharide of claim 1, wherein said chitosan moieties are homopolymers of glucosamine.

5. The chitosan-containing polysaccharide of claim 1, wherein the glucan moieties are homopolymers of glucose.

6. A method for the preparation of a chitosan-containing polysaccharide as set forth in claim 1, comprising:
   (a) heat-treating a fungus in an aqueous caustic alkali solution, wherein said aqueous caustic alkali solution has a concentration ranging from 25 to 50% by mass;
   (b) subjecting the solution of (a) to a solid-liquid separation treatment;
   (c) dissolving the solid of (b) in an aqueous organic acid solution;
   (d) forming a precipitate from the solution of (c) by adding an alcohol or a caustic alkali to the solution of (c) and adjusting the pH of the resulting solution to a pH value of not less than 10;
   (e) washing the precipitate of (d); and
   (f) drying the precipitate of (e).

7. The method for the preparation of a chitosan-containing polysaccharide as set forth in claim 6, wherein the fungus is pre-treated with a cellulase or glucanase, prior to the heat-treatment thereof in the aqueous caustic alkali solution.

8. The method for the preparation of a chitosan-containing polysaccharide as set forth in claim 6 or 7, wherein the fungus is *Agaricus bisporus*.

9. A method for the preparation of a chitosan-containing polysaccharide as set forth in claim 1, comprising:
   (a) heat-treating a fungus in an aqueous caustic alkali solution, wherein said aqueous caustic alkali solution has a concentration ranging from 25 to 50% by mass;
   (b) adjusting viscosity of the solution of (a) to a level of 3 to 20 mPa·s;
   (c) subjecting the solution of (b) to a solid-liquid separation treatment;
   (d) washing the solid obtained from (c); and
   (e) drying the solid of (d).

10. The method for the preparation of a chitosan-containing polysaccharide as set forth in claim 9, wherein said viscosity is adjusted to a level of 3 to 20 mPa·s.

11. A pharmaceutical composition comprising, as an effective component, a chitosan-containing polysaccharide as set forth in claim 1.

12. A food comprising a chitosan-containing polysaccharide as set forth in claim 1.

13. A method for treatment of hypertension in a subject, comprising administering to a subject in need of such treatment a chitosan-containing polysaccharide as set forth in claim 1.

14. A method for treatment of diabetes in a subject, comprising administering to a subject in need of such treatment a chitosan-containing polysaccharide as set forth in claim 1.

15. A method for lowering blood pressure in a subject, comprising administering to a subject in need of such lowering a chitosan-containing polysaccharide as set forth in claim 1.

16. A method for lowering urine-sugar levels in a subject, comprising administering to a subject in need of such lowering a chitosan-containing polysaccharide as set forth in claim 1.

17. A method for lowering uric acid levels in a subject, comprising administering to a subject in need of such lowering a chitosan-containing polysaccharide as set forth in claim 1.

18. A method for lowering an overall cholesterol level in a subject, comprising administering to a subject in need of such lowering a chitosan-containing polysaccharide as set forth in claim 1.

19. A method for lowering neutral fat levels in a subject, comprising administering to a subject in need of such lowering a chitosan-containing polysaccharide as set forth in claim 1.

* * * * *